US007664661B2

(12) United States Patent
Schwalb et al.

(10) Patent No.: US 7,664,661 B2
(45) Date of Patent: Feb. 16, 2010

(54) ELECTRONIC METHOD AND SYSTEM THAT IMPROVES EFFICIENCIES FOR RENDERING DIAGNOSIS OF RADIOLOGY PROCEDURES

(75) Inventors: Perry L. Schwalb, Metairie, LA (US);
Eric S. Schulze, Metairie, LA (US);
Jonah H. Still, New Orleans, LA (US)

(73) Assignee: Avreo, Inc., North Charleston, SC (US)

( * ) Notice: Subject to any disclaimer, the term of this patent is extended or adjusted under 35 U.S.C. 154(b) by 0 days.

(21) Appl. No.: 12/069,468

(22) Filed: Feb. 11, 2008

(65) Prior Publication Data

US 2008/0208634 A1     Aug. 28, 2008

Related U.S. Application Data

(63) Continuation of application No. 09/726,475, filed on Nov. 30, 2000, now abandoned.

(60) Provisional application No. 60/168,106, filed on Nov. 30, 1999.

(51) Int. Cl.
*A61B 5/00* (2006.01)

(52) U.S. Cl. .................. 705/3; 600/443; 382/128; 707/104.1; 378/63

(58) Field of Classification Search ................ 705/3; 600/443; 382/128; 707/104.1; 378/63
See application file for complete search history.

(56) References Cited

U.S. PATENT DOCUMENTS

| 5,177,775 | A |   | 1/1993  | Onodera       |        |
|-----------|---|---|---------|---------------|--------|
| 5,321,520 | A |   | 6/1994  | Inga et al.   |        |
| 5,361,202 | A |   | 11/1994 | Dowe          |        |
| 5,416,602 | A |   | 5/1995  | Inga et al.   |        |
| 5,452,416 | A |   | 9/1995  | Hilton et al. |        |
| 5,513,101 | A | * | 4/1996  | Pinsky et al. | 705/3  |
| 5,542,003 | A |   | 7/1996  | Wafford       |        |
| 5,668,998 | A |   | 9/1997  | Mason et al.  |        |
| 5,671,353 | A |   | 9/1997  | Tian et al.   |        |
| 5,680,471 | A |   | 10/1997 | Kanebako      |        |
| 5,734,915 | A |   | 3/1998  | Roewar        |        |
| 5,818,901 | A | * | 10/1998 | Schulz        | 378/63 |
| 5,867,821 | A |   | 2/1999  | Ballantyne et al. |    |

(Continued)

OTHER PUBLICATIONS

Fundamentals of Radiology CD-ROM from the Radiology Department of Dalhousie University; Cupido Daniels, Editor, JAMA, Aug. 13, 197, pp. 1-3.

*Primary Examiner*—Vanel Frenel
(74) *Attorney, Agent, or Firm*—Jones, Walker, Waechter, Poitevent, Carrere & Denegre, LLP

(57) ABSTRACT

An electronic method and system for improving radiologists' efficiencies when viewing radiology procedures and rendering diagnosis in a manner that emulates current methods and apparatus. The method of the present invention includes reviewing electronic radiology images and reports contained in a patient's digital master folder (an information object invented to manage the patient's radiology information), comparing images from the current procedure to specific images from prior procedures in a specified order, and dictating the procedure's diagnosis into the digital master folder. The apparatus of the present invention includes a flat panel monitor for the viewing and manipulation of digital master folders, a dictation trackball device for manual and voice enabled operation and navigation of the system, and multiple high-resolution computer monitors functioning as a "lightbox" for the viewing of radiology images.

28 Claims, 13 Drawing Sheets

U.S. PATENT DOCUMENTS

| | | |
|---|---|---|
| 5,897,498 A | 4/1999 | Canfield |
| 5,903,889 A | 5/1999 | de la Hoerga |
| 5,911,687 A | 6/1999 | Sato et al. |
| 5,915,240 A | 6/1999 | Karpf |
| 5,924,074 A | 7/1999 | Evans |
| 5,993,391 A | 11/1999 | Kamiyama |
| 6,047,081 A | 4/2000 | Graezinger et al. |
| 6,183,139 B1 | 2/2001 | Solomon et al. |
| 6,243,095 B1 | 6/2001 | Shile et al. |
| 6,260,049 B1 * | 7/2001 | Fitzgerald et al. ........ 707/104.1 |
| 6,272,470 B1 | 8/2001 | Teshima |
| 6,417,870 B1 | 7/2002 | Brackett et al. |
| 6,549,214 B1 | 4/2003 | Patel et al. |
| 6,640,145 B2 | 10/2003 | Hoffberg et al. |
| 2001/0018659 A1 | 8/2001 | Koritzinsky |

* cited by examiner

FIG. 1

AVREO

DEPARTMENT OF RADIOLOGY
338 Camp Street - Suite 400
New Orleans, Louisiana 70130
(800) 844-9925

| | | | |
|---|---|---|---|
| Patient Name: | RAIN, MIKE | Referring Physician: | BAKER, STEVE |
| X Ray Number: | 4640 | MRN: | |
| Sex: | M | Study Date: | 11/28/2000 |
| DOB: | 4/14/1922 | Admission Date: | |
| Age: | 78 | Patient Type: | |

Exam: US   Date Performed: 11/28/2000   Time Performed: 13:00:00

Indication
Right carotid bruit.

Procedure
Color flow Doppler evaluation of the extracranial carotid circuit was performed.

Findings
The right common carotid artery demonstrates intimal thickening with flow velocity during systole measuring 66.3 cm per second. The right internal carotid artery also demonstrates intimal thickening with flow velocity during systole measuring 34.4 and during diastole 6.1 cm per second. The ratio of right internal right common primary flow velocities during systole is .5 which is consistent with the mild degree of stenosis (1 - - 39 percent). The left common carotid artery demonstrates intimal thickening within the vessel wall with a flow velocity during systole measuring 82.8 cm per second. Left internal coronary artery also demonstrates intimal thickening with a flow velocity during systole measuring 62 and during diastole 15.5 cm per second. The ratio of left internal left common carotid artery flow velocities during systole is .7 which is consistent with a mild degree of stenosis (1 - - 39 percent). Antegrade flow is given the vertebral arteries bilaterally.

Impression
1. Bilateral internal carotid arteries: mild degree of stenosis (1 - - 39 percent) within both vessels due to minimal arteriosclerotic vascular changes.

Reading Physician:

Listen to dictated Report —— 15

*FIG. 2*

ELECTRONIC METHOD AND SYSTEM THAT IMPROVES EFFICIENCIES FOR RENDERING DIAGNOSIS OF RADIOLOGY PROCEDURES

CROSS-REFERENCE TO RELATED APPLICATIONS

This application is a continuation of and claims the benefit of U.S. Non-Provisional patent application Ser. No. 09/726,475 filed Nov. 30, 2000, which further claims the benefit of U.S. Provisional Application No. 60/168,106 filed Nov. 30, 1999. The subject matter of those applications is incorporated by this reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a method and apparatus for improving radiologists' efficiencies when viewing radiology procedures and rendering diagnosis.

2. General Background of the Invention

Typically, every radiology office uses a dictating machine for the preparation of reports, a stack of master folders that contain patient information, and a light box, roto viewer, or like device for viewing radiology images. These images can include for example x-rays, ultrasound, magnetic resonance imaging (MRI), computer tomography, nuclear medicine images and the like.

The manual file folder system employed by radiologists and radiology departments is inefficient and cumbersome.

BRIEF SUMMARY OF THE INVENTION

The present invention provides an electronic method of improving the efficiency of a radiologist and of a radiology department.

With the present invention, a plurality of computer monitors are provided for displaying various images. At least one of the monitors simulates a radiology "light box", roto viewer, or like device for displaying electronic radiology images.

At least one of the monitors is used to display a digital graphical representation of a patient's folder, namely a digital master folder.

A hyperlink is used to open the report and to open different "pages" of the patient's master folder.

In one embodiment, a voice activated command can be used to open the patient's master folder or to open "pages" of the patient's folder.

In another embodiment, a track ball device such as a computer mouse can be used to open the patient's master folder or "pages" contained within the folder.

In another embodiment, the radiologist/user is provided with a combination microphone/track ball device that enables the radiologist or user to open the patient's master folder or components thereof using either voice activated commands or the track ball device. A touch screen device hyperlink can also be used to open a patient's folder or report.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 1 is a screen capture image showing a patient's radiology master folder that displays basic patient information including name, number, and study date;

FIG. 2 is a screen capture image showing the report, displayed by double clicking on the report hyperlink;

DETAILED DESCRIPTION OF THE INVENTION

Figure 1:
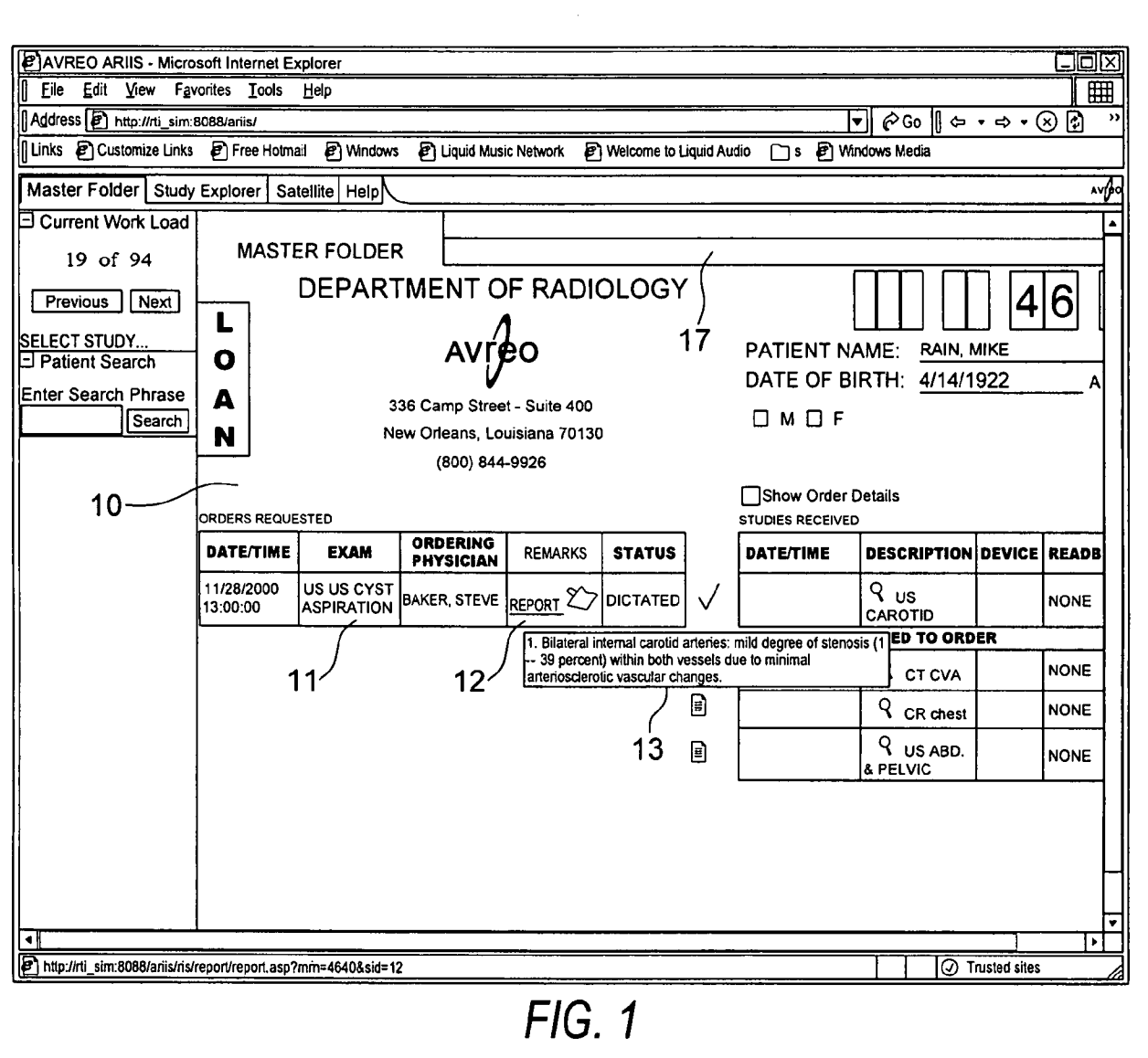
Figure 3:
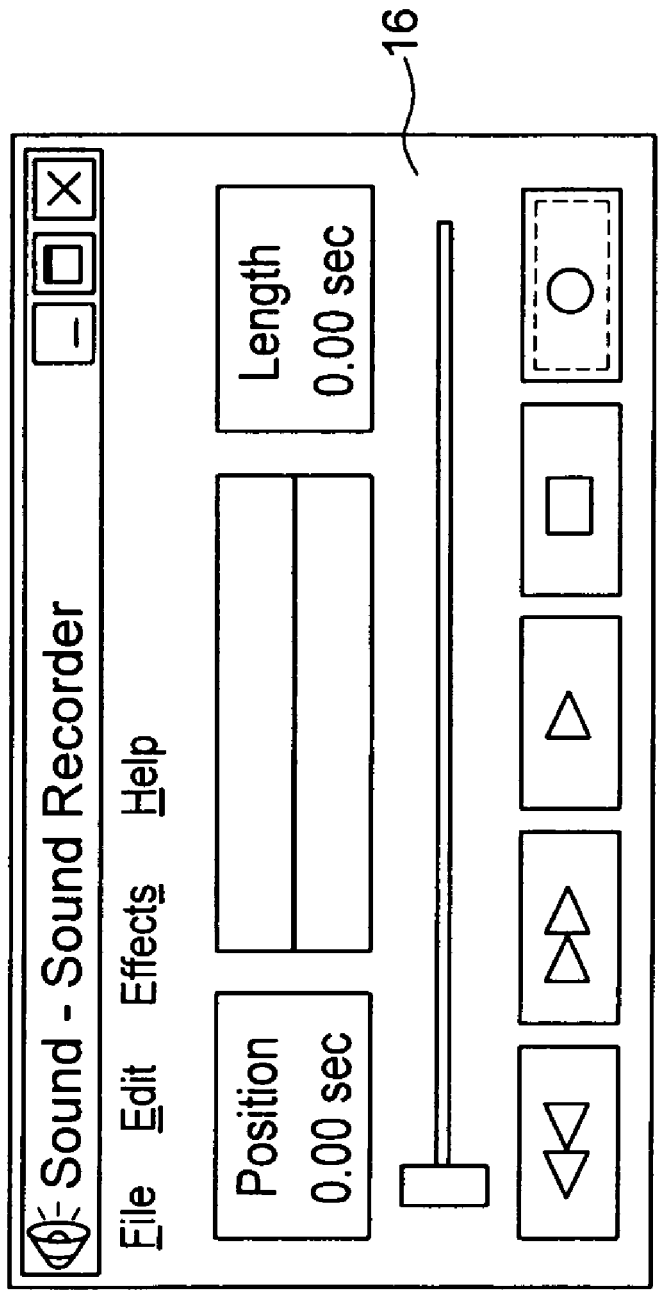
FIG. 3 is a screen capture image showing the audio graphical display generated by the audio hyperlink 15.

FIG. 1 shows a digital representation of a patient folder designated generally by the numeral 10. Patient folder 10 shows two hyperlinks 11, 12. At the top center of the folder 10, a header 17 indicates that this folder can, for example, relate to an ultrasound. The folder could relate to their radiology procedures. By clicking on the ultrasound hyperlink, the window shown in FIG. 1 is opened providing a report display area 13 to be filled with the report information in text form as dictated by a radiologist.

When a radiologist double clicks on the report hyperlink 12 in FIG. 1, the screen in FIG. 2 is displayed which is the report screen 14 containing patient information and the substance of the report. Audio hyperlink 15 can be double clicked using the computer mouse in order to actually hear the report. When a user double clicks on the hyperlink 15 in FIG. 2, the display in FIG. 3 is shown on the screen having a graphical display for the audio.

Figure 4:
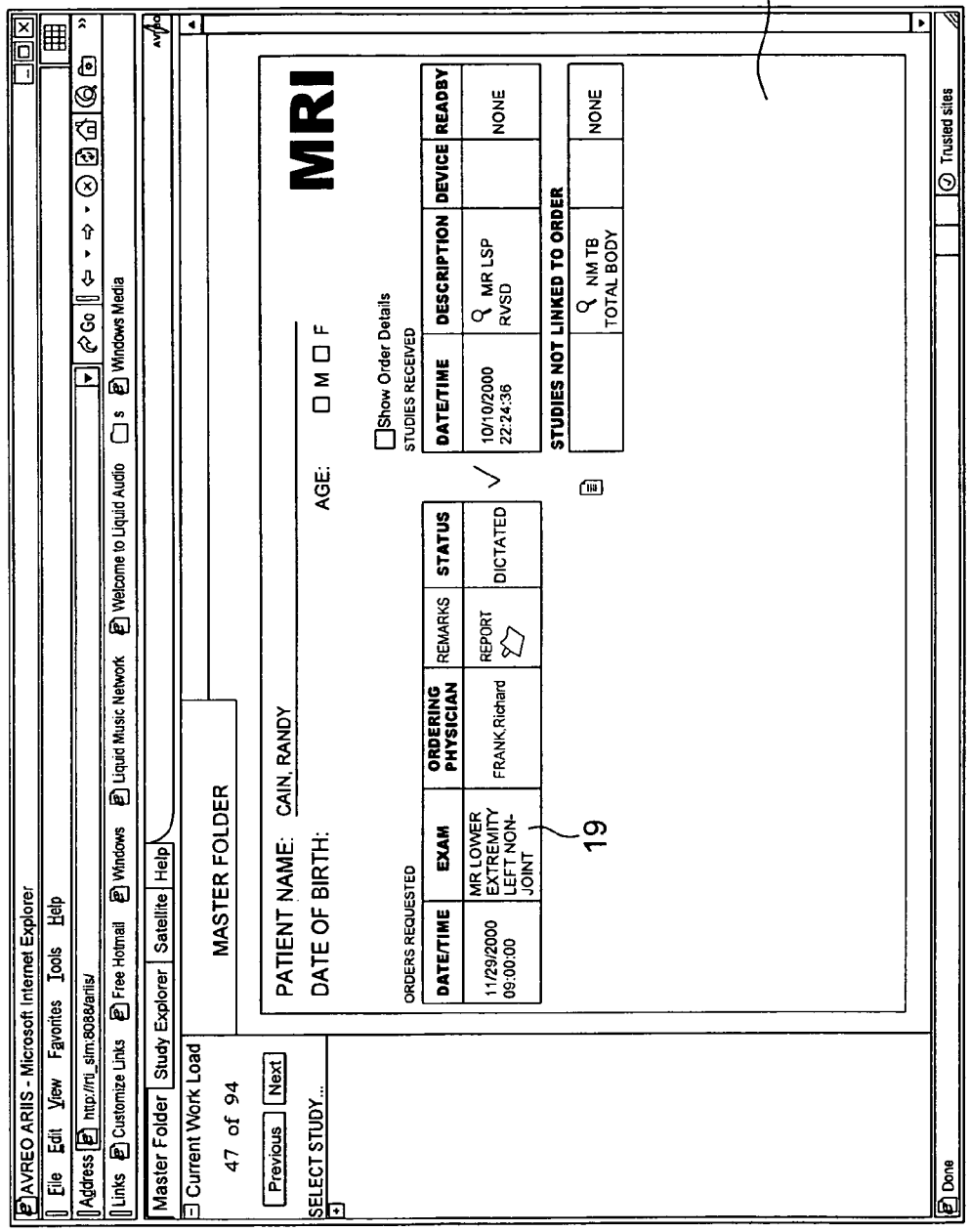
FIG. 4 is a screen capture image showing a modality subfolder generated by double clicking on the ultrasound header 17.

When the radiologist double clicks on the ultrasound header 17 in FIG. 1, the screen provided in FIG. 4 has a modality subfolder 18 having a hyperlink 19. When the radiologist uses the computer mouse to double click on the exam hyperlink in FIG. 4, actual radiology images as shown in FIG. 5 are displayed.

Figure 5:
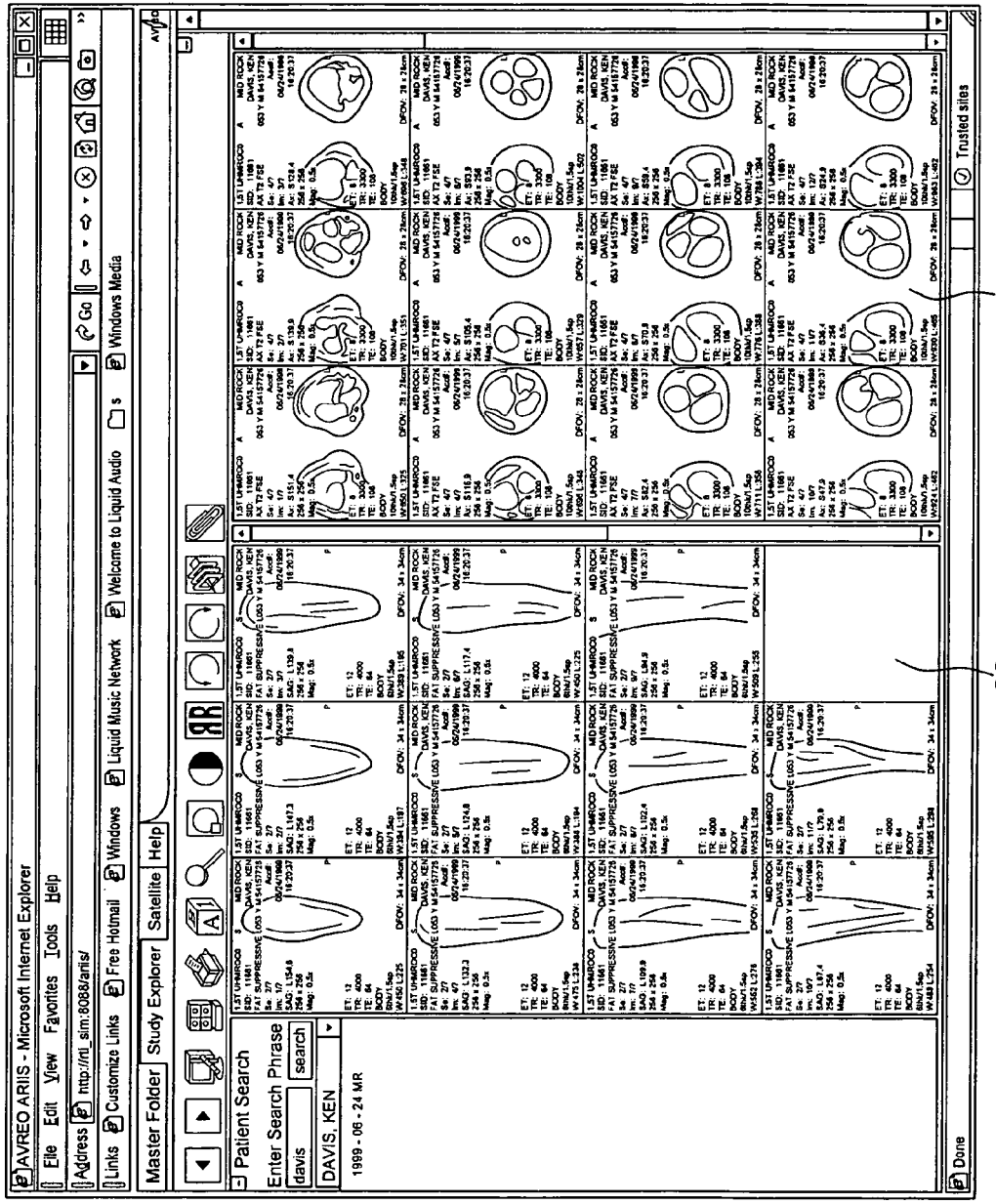
FIG. 5 is a screen capture image that shows radiology images in twelve up format.
Figure 6:
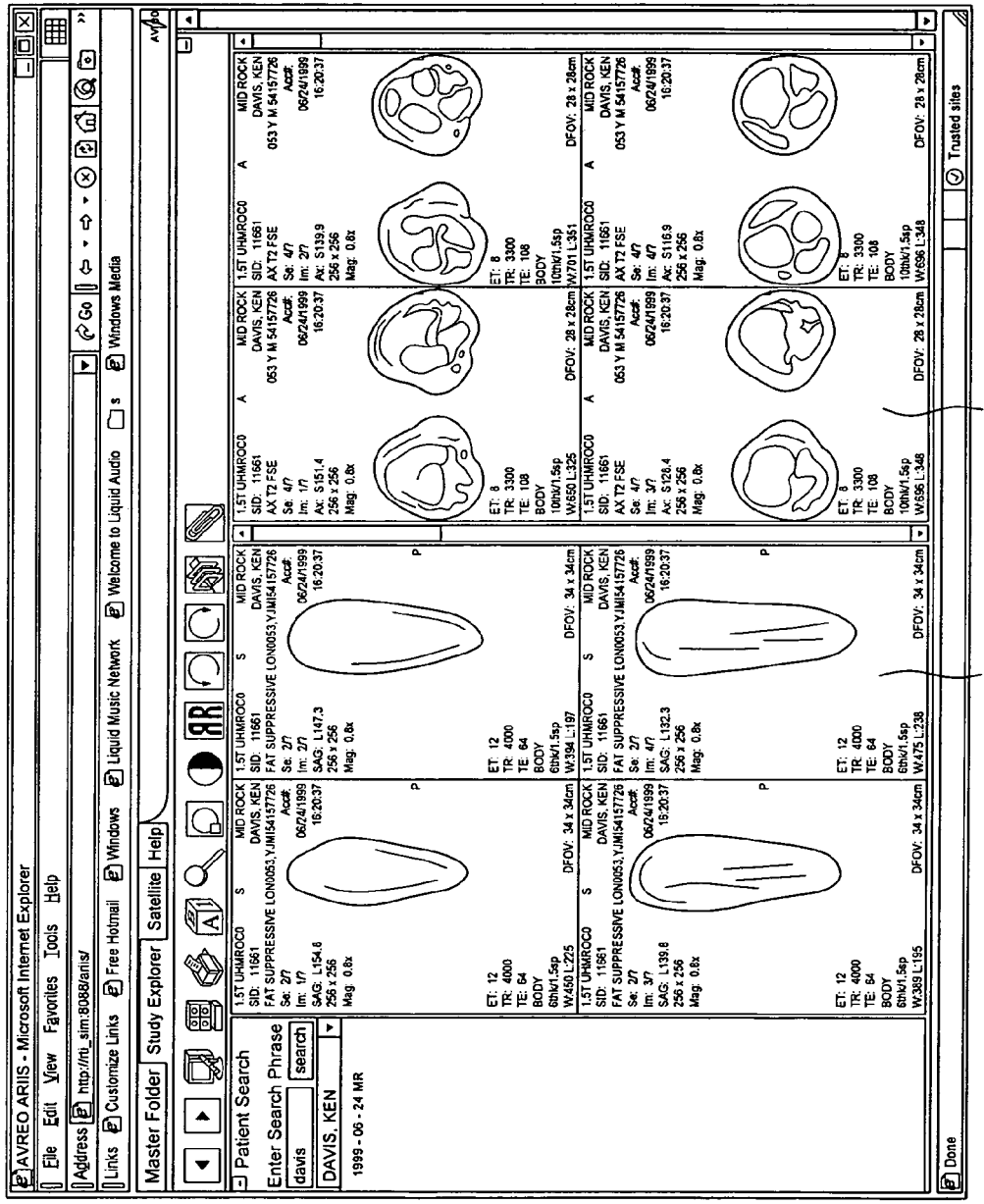
FIG. 6 is a screen capture image that shows radiology images in four up format.
Figure 7:
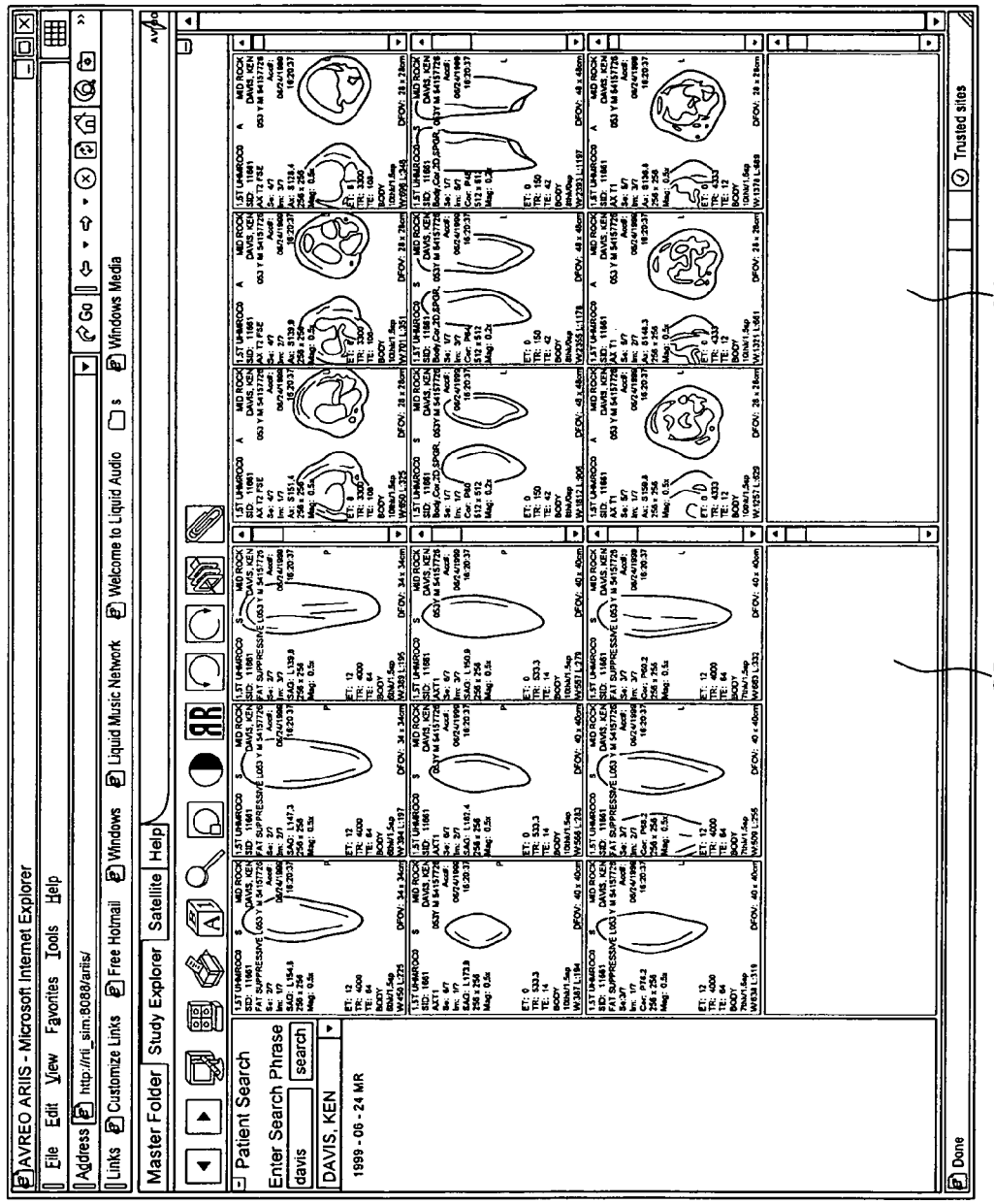
FIG. 7 is a screen capture image that shows radiology images in cine mode.
Figure 8:
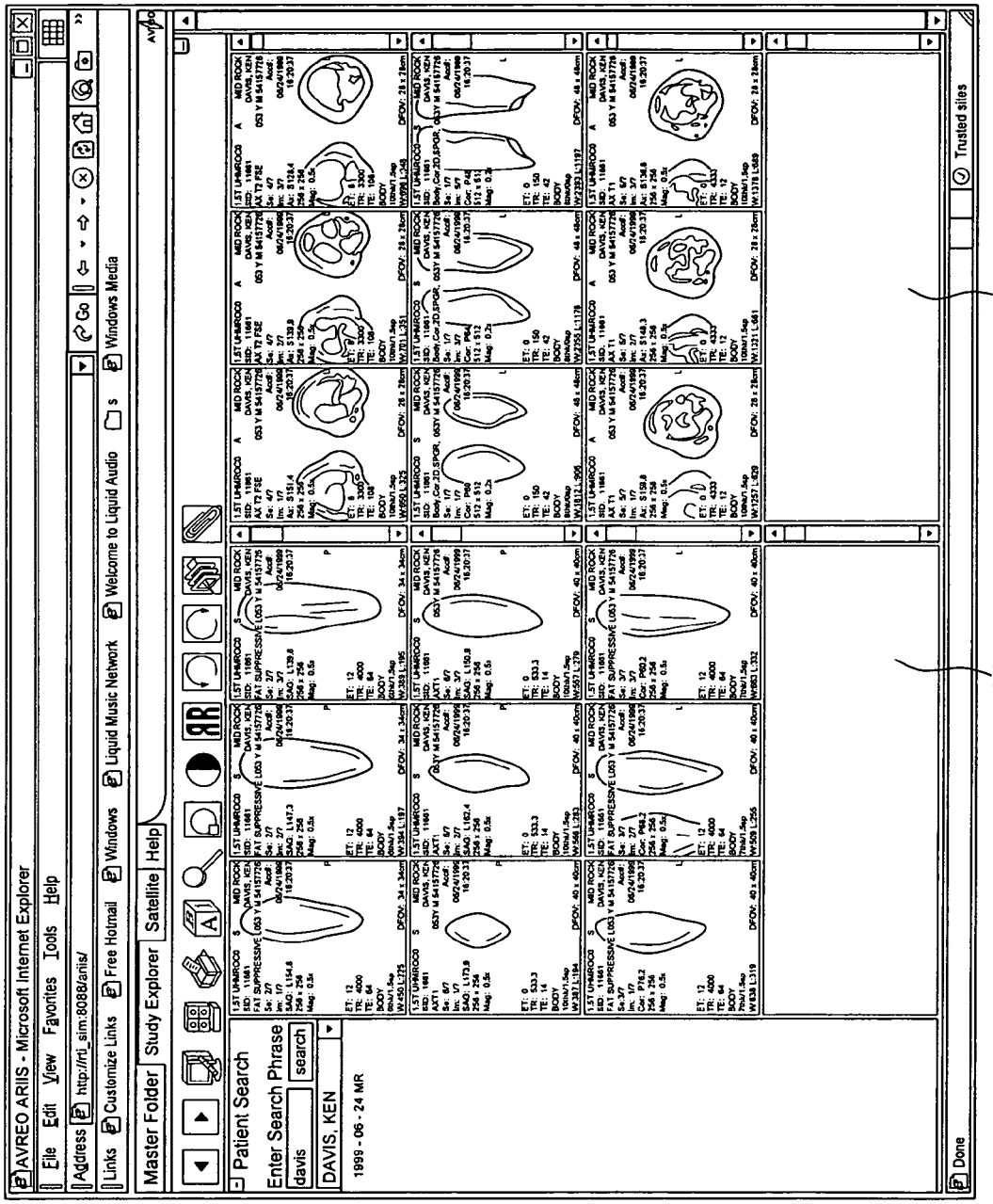
FIG. 8 is a screen capture image that shows a cine set display.

In FIG. 5, a left computer monitor 20 and a right computer monitor 21 are shown. In FIG. 5, a "twelve up" configuration is shown in each of the monitors 20, 21. In FIG. 6, a "four up" configuration is shown in each of the monitors 20, 21. In FIG. 7, a cine mode is shown for each of the monitors 20, 21. In the cine mode, sets of images are grouped and maintained in that grouping on a selected screen 20 or 21. FIG. 8 is a screen capture image that shows a cine set display.

Figure 9:
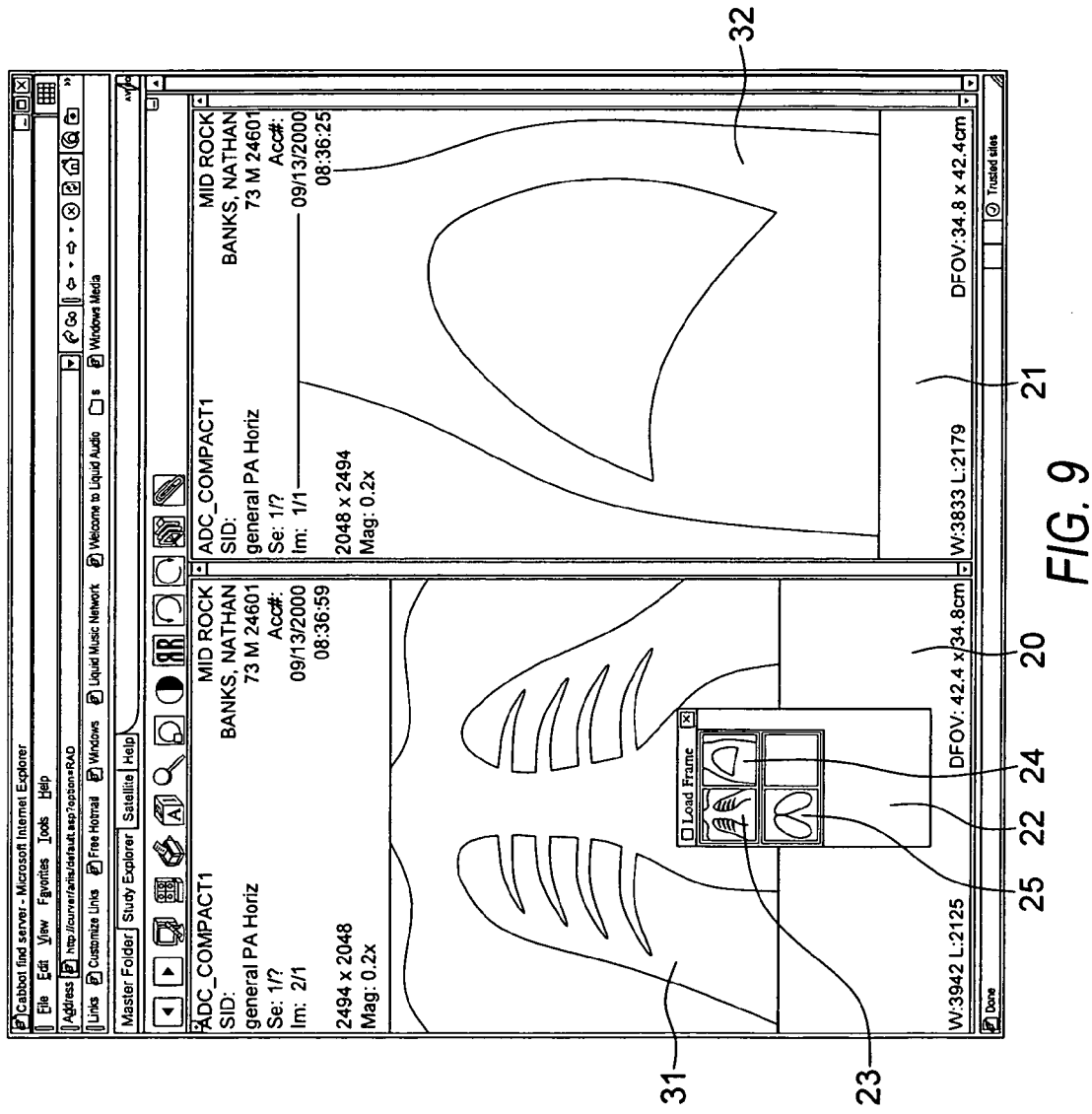
FIG. 9 is a screen capture image that shows radiographic images, showing current chest x-rays views, on the two high resolution monitors with the roto viewer window displayed.

FIGS. 9-12 show the use of the method and apparatus of the present invention to display full size radiology images, namely one image per screen 20, 21. In FIG. 9, as an example, image 31 is a left image, current PA for a patient. The right image in FIG. 9 is an image that is a current lateral for the patient. To the left hand side in the screen capture of FIG. 9, a roto viewer 22 is also shown. The roto viewer in FIG. 9 is comprised of two columns of boxes, each column containing a set of windows, each window can be designated by the numeral 25. The windows 25 can be scrolled to display various radiology images as further shown in FIGS. 9 and 10.

Figure 10:
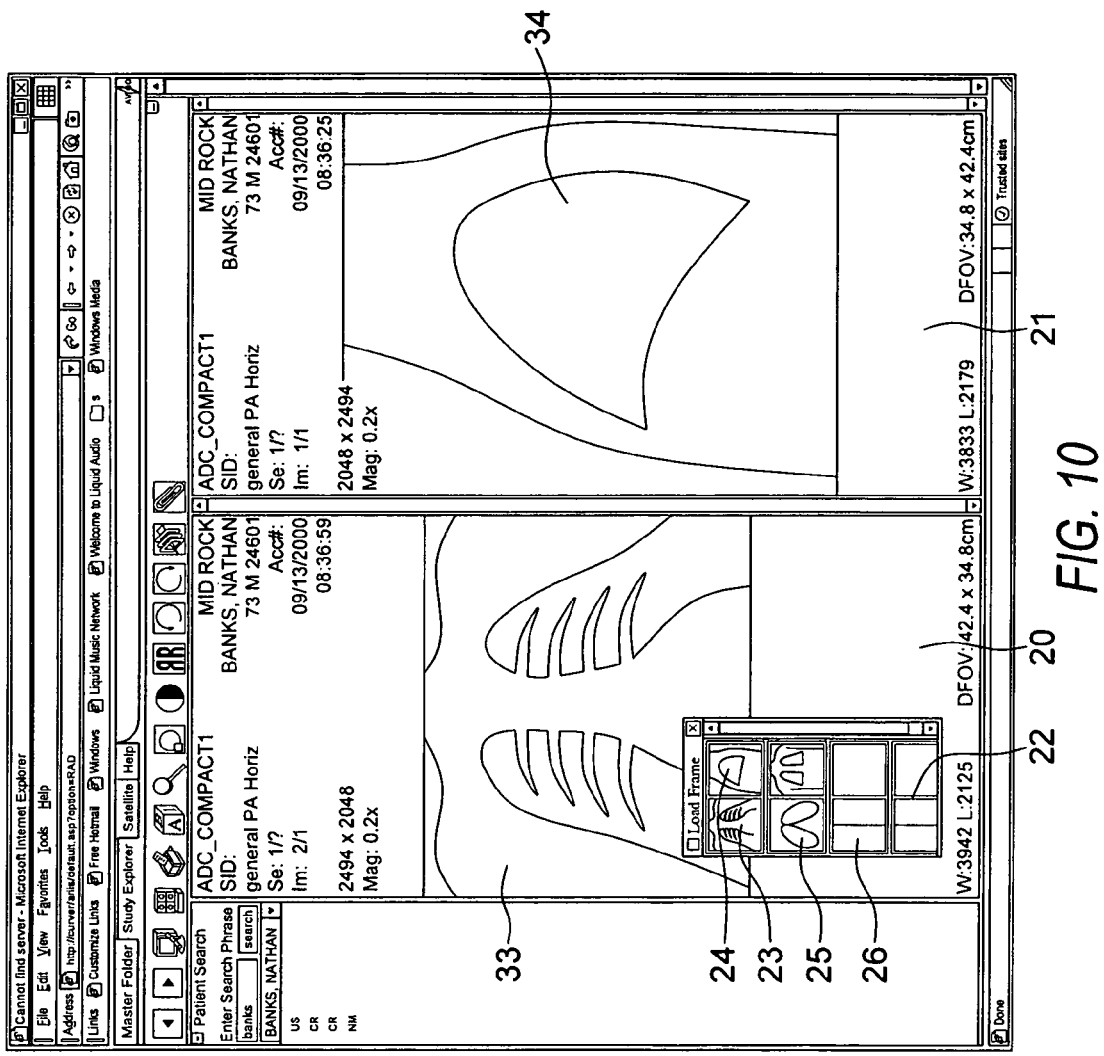
FIG. 10 is a screen capture image that shows chest x-ray views current and most recent with the roto viewer window displayed.

In FIGS. 9 and 10, the upper left window box of roto viewer 22 is designated by the numeral 23. The upper right window box is designated by the numeral 24. The screen captures of FIGS. 9 and 10 illustrate examples of radiology images that can be displayed using the method and apparatus of the present invention.

As shown in FIG. 10, the roto viewer 22 can include different groups of images in each of the window boxes 23, 24, 25 or 26. In FIG. 10, the window 23 contains those images which are displayed in the left hand computer monitor 20. The window box 24 of roto viewer 22 contains images which are displayed in the right hand monitor 21 in FIG. 10. Other images can be contained in other window boxes of the roto viewer 22 as shown in FIG. 10, just below window boxes 23, 24. Each of these images 33, 34 appear in the roto viewer window boxes 23, 24. The roto viewer 22 can be moved about the screen by dragging it.

Figure 11:
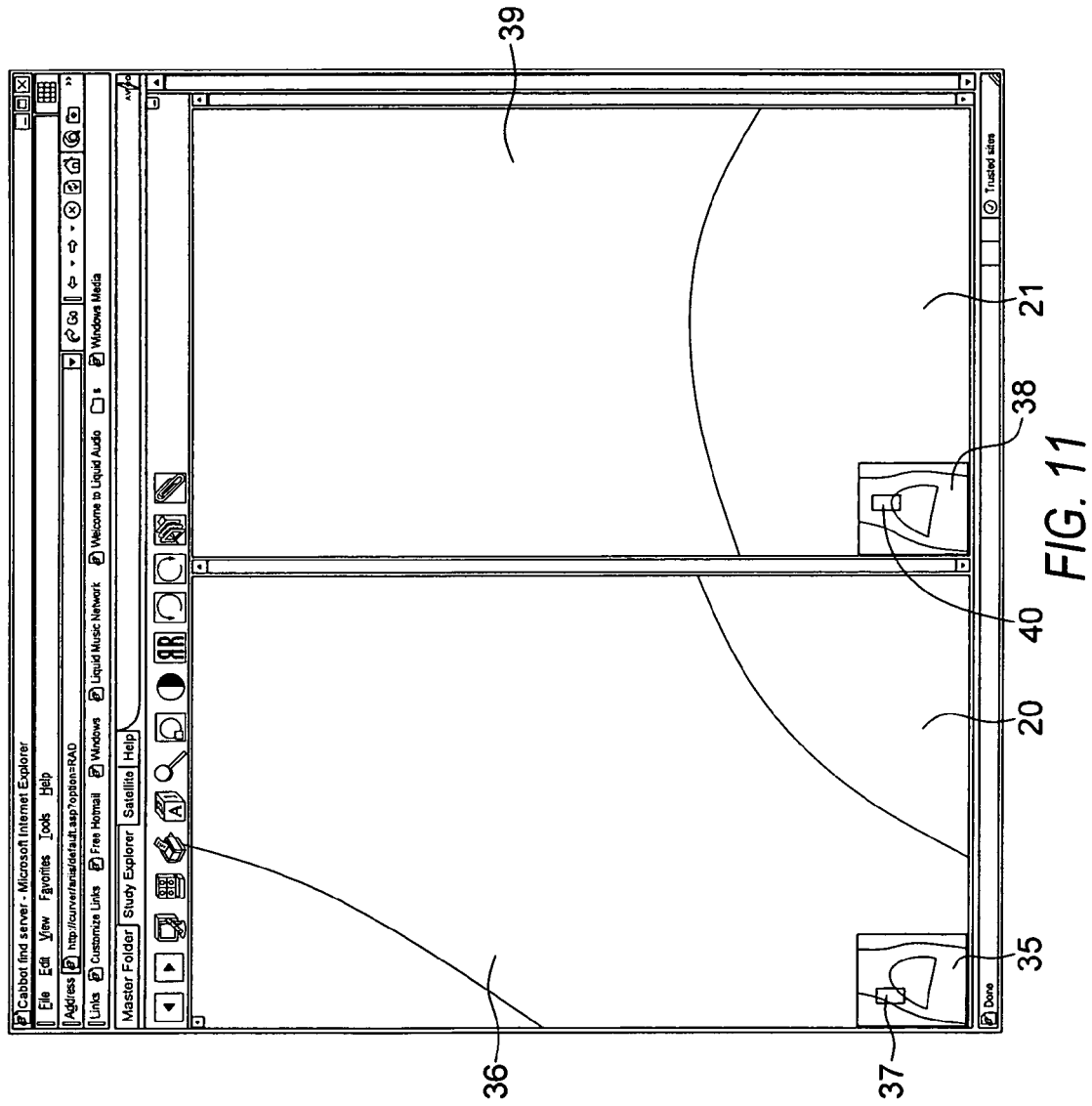
FIG. 11 is a screen capture image that shows radiographic images demonstrating picture zoom.

In FIG. 11, the zoom feature of the present invention is illustrated. Each of the screens 20, 21 display a zoomed image. The monitor 20 displays image 36. The monitor 21 displays image 39. At the lower left hand corner of each of the screens 20, 21, there is provided a picture in a picture display. This picture in a picture display includes the smaller picture 35 showing a chest x-ray as an example. The viewing area 37 represents that portion of the chest x-ray 35 that is to be displayed in zoom format as image 36 in FIG. 11. Similarly, the monitor 21 displays at its lower left hand corner a picture in picture 38 having viewing area 40 that designates the zoom area of the chest x-ray 38. The image 39 is that portion of the image contained within viewing area 40 and which has been enlarged to fill substantially all of screen 21.

Figure 12:
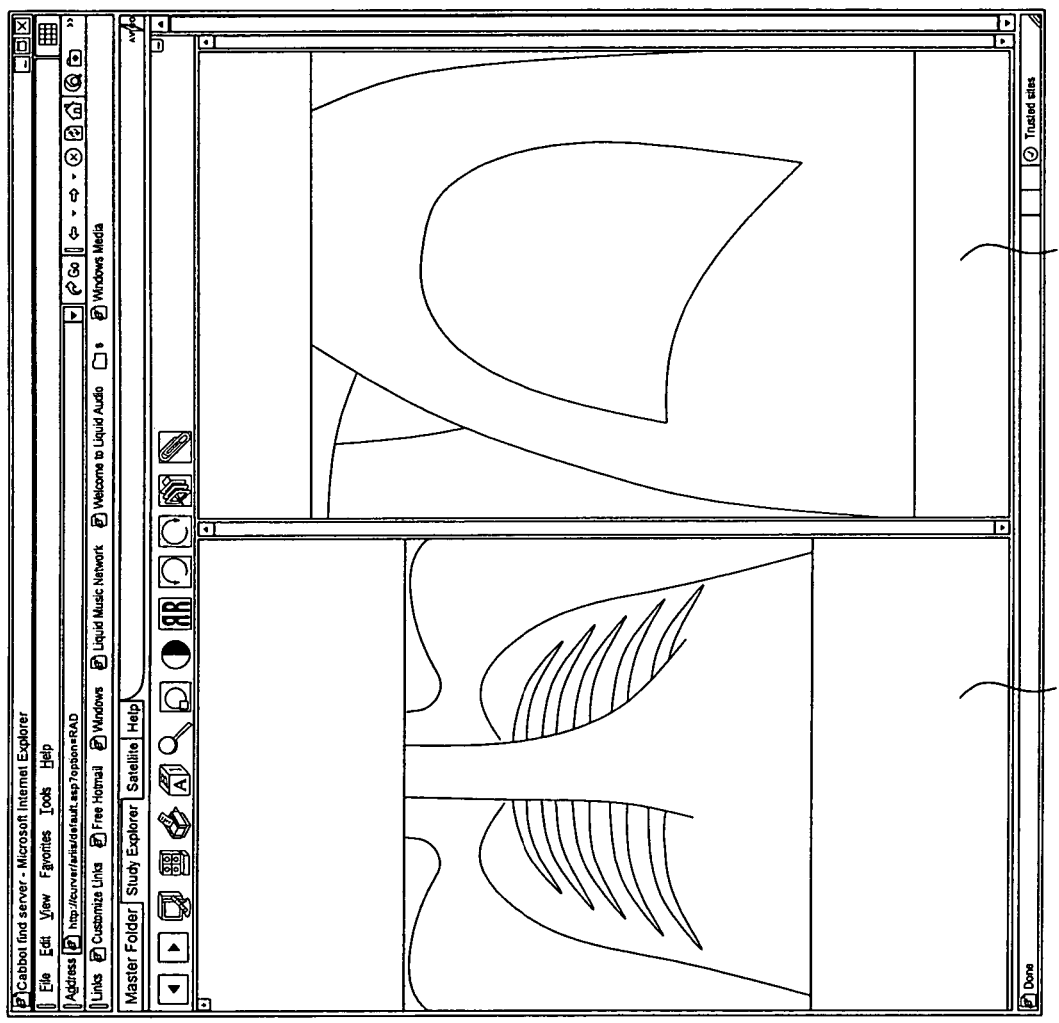
FIG. 12 is a screen capture image showing radiographic images without the roto viewer.

FIG. 12 illustrates monitors 20, 21 with the roto viewer 22 removed.

Figure 13:
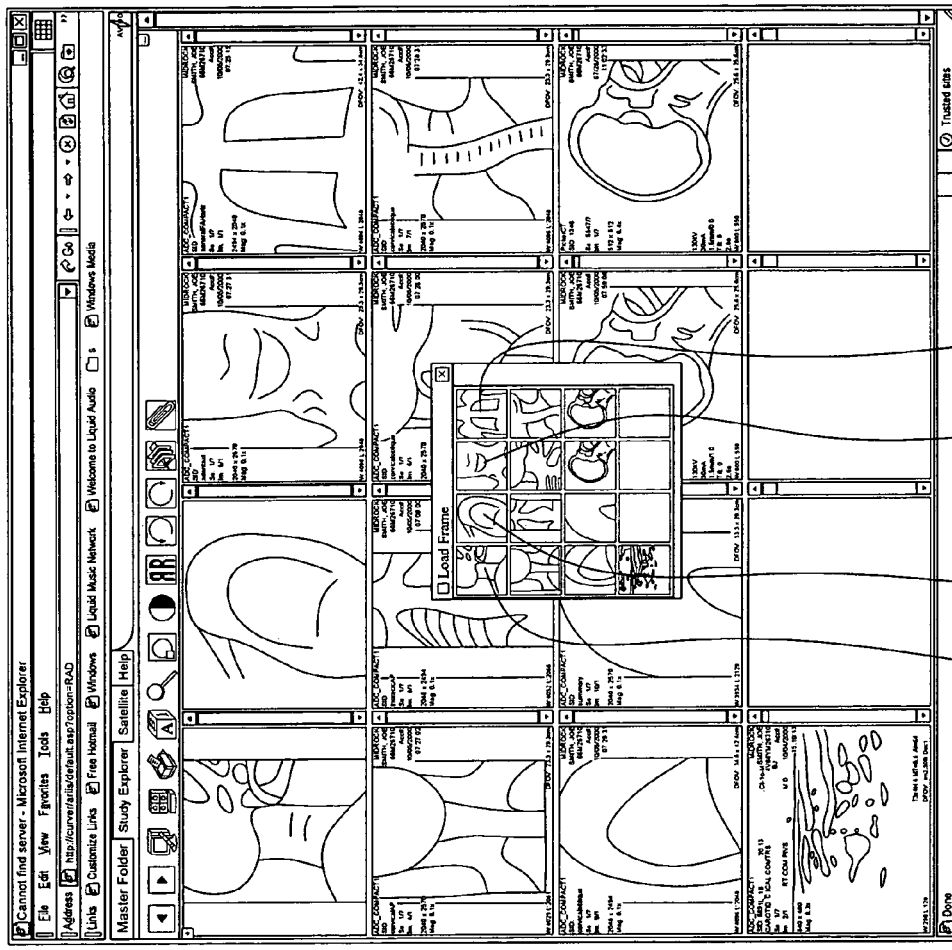
FIG. 13 is a screen capture image showing multiple images using the roto viewer.

In FIG. 13, the group of windows 27, 28, 29 and 30 represent different cine sets or groups of images that have been purposely grouped together by the radiologist. Each of the windows 27-30 can be moved about within the roto viewer to move the displayed images around the screens 20, 21.

PARTS LIST

| Part No. | Description |
|---|---|
| 10 | folder |
| 11 | hyperlink (ultrasound) |
| 12 | hyperlink (report) |
| 13 | report display area |
| 14 | report |
| 15 | audio hyperlink |
| 16 | graphical display - audio |
| 17 | ultrasound header |
| 18 | modality subfolder |
| 19 | hyperlink |
| 20 | left monitor |
| 21 | right monitor |
| 22 | roto viewer |
| 23 | left window box |
| 24 | right window box |
| 25 | windows/roto viewer |
| 26 | windows/roto viewer |
| 27 | windows group |
| 28 | windows group |
| 29 | windows group |
| 30 | windows group |
| 31 | left image/current PA |
| 32 | right image/current lateral |
| 33 | left image/current PA |
| 34 | right image/most recent lateral |
| 35 | picture in picture |
| 36 | image - zoom |
| 37 | view area |
| 38 | picture in picture |
| 39 | image - zoom |
| 40 | view area |

The foregoing embodiments are presented by way of example only; the scope of the present invention is to be limited only by the following claims.

The invention claimed is:

1. An electronic method of improving the efficiency of a radiologist, comprising the steps of:
 a) providing a system that includes a computer and a plurality of monitors interfaced with the computer, each monitor for displaying an image;
 b) using at least one of the monitors to simulate a radiology "light box" for displaying electronic radiology images;
 c) using at least one of the monitors to simulate a digital graphical representation of a patient's manual master folder comprising the steps of:
  (i) generating by a specialized software application the digital graphical representation of the patient's manual master folder as an image on the monitor specifically designed for use as a graphical user interface by the radiologist;
  (ii) generating data fields on the digital graphical representation including patient information, medical procedures information and radiologist information regarding all radiology procedures associated with such patient stored in an information database;
  (iii) providing information and hyperlinks to radiology reports and images in an electronic layout and color scheme conforming to the layout and color scheme of the patient's manual master folder and tailored to a radiologist practice; and
  (iv) including hyperlinks within at least one data field to view additional information or images relating to a patient's medical records when clicked;
 d) using a hyperlink to open the folder displayed in step "c" to display information contained in the folder; and e) using a hyperlink that accesses the folder to display a current radiology image from a current radiology procedure being performed on the patient to permit diagnosis.

2. The method of claim 1 wherein in step "d" a voice activated command is used to open the patient's master folder.

3. The method of claim 1 wherein in step "d" a trackball device is used to open the patient's master folder.

4. The method of claim 1 further comprising the step of providing a combination dictation and trackball device, and wherein in step "d" a user can selectively use either a voice activated command or a trackball to open the patient's master folder.

5. The method of claim 1 further comprising the step of using the computer to interface the monitors and the hyperlink.

6. The method of claim 4 further comprising the step of using the computer to interface the monitors and the combination dictation and trackball device.

7. The method of claim 1 wherein there are two monitors in step "c" that are used to display electronic radiology images.

8. The method of claim 1 wherein the monitor in step "c" that is used to display electronic radiology images is a high resolution monitor.

9. The method of claim 7 wherein the monitors in step "c" that are used to display electronic radiology images is a high resolution monitor.

10. The method of claim 1 wherein in step "b" the image viewed is an ultrasound image.

11. The method of claim 1 wherein in step "b" the image viewed is a magnetic resonance image.

12. The method of claim 1 wherein in step "b" the image viewed is a computer tomography image.

13. The method of claim 1 wherein in step "b" the image viewed is a computer radiology image.

14. The method of claim 1 wherein in step "b" the image viewed is a nuclear medicine image.

15. A method for reviewing electronic radiology information including patient demographics, radiology procedures, radiology reports and radiology images, comprising the steps of:
   a) loading the radiology information associated with a selected group of patients that are assigned to a selected radiologist into a computer memory;
   b) generating by a specialized software application an image of a radiology manual master folder on an area of a computer display for use as a graphical user interface by the radiologist;
   c) generating data fields associated with a digital master folder on the image of a patient's manual master folder including patient's name, medical record number, date of birth, sex, and information regarding all procedures associated with such patient stored in an information database including date, type of procedure, report, and radiologist, the digital master folder specifically designed for use by a radiologist;
   d) displaying the information associated with the patient from computer memory in data fields on the computer display in an electronic layout and color scheme conforming to the layout and color scheme of the patient's manual master folder;
   e) providing hyperlinks within the procedure and report data fields to view additional information or images relating to a patient's medical records when clicked, the information and images displayed in electronic formats and configurations tailored to a radiology practice;
   f) clicking on the report field, displays a new window that contains the text of the report and a link to the digitally recorded dictation of the report, that when clicked will play the recording;
   g) placing a cursor over the report field on the digital master folder, to display summary information of the report;
   h) clicking on the procedure field to send a command to a viewing portal to load all of the procedures and images that meet the criteria of the radiologist's file;
   i) viewing current radiology images from a current radiology procedure being performed on the patient together with images from prior radiology procedures;
   j) generating a searchable and selectable list of patients that have procedures assigned to the radiologist on the computer display; and
   k) providing commands that navigate through the stack of master folders, displaying information associated with a new patient in a data field on the computer display from computer memory.

16. An apparatus to access, store, and distribute electronic radiology information including patient demographics, radiology procedures, radiology reports and radiology images comprising:
   a) an information data base including patient demographics, radiology identification number, procedures, images, reports, orders and appointments;
   b) means for transmitting and receiving the information between computers connected to a computer network via extensible markup language (XML);
   c) means for searching for a plurality of user specified types of information contained in the information data base;
   d). means for generating by a specialized software application a digital master folder representation of a patient's manual master folder for displaying the specified types of information over a monitor of a computer connected to the computer network, the digital master folder representation specifically designed for use as a graphical user interface by a radiologist;
   e). means for generating data fields on the digital master folder representation including radiology reports and images information regarding all radiology procedures associated with such patient stored in the information database;
   f). means for viewing current radiology images from a current radiology procedure being performed on the patient;
   g). means for displaying the radiology reports and images in an electronic layout and color scheme conforming to the layout and color scheme of the patient's manual master folder and tailored to a radiology practice; and
   h). means for providing hyperlinks within at least one data field to view additional information or images relating to a patient's medical records when clicked.

17. A multi-monitor radiology image viewing system comprising:
   a) a plurality of monitors;
   b) a combination dictation and trackball device that includes a hyperlink to view a patients' information and medical images on separate monitors comprising:
   c) a radiology portal that includes a monitor and a computer for the searching and that includes viewing medical information, the medical information displayed over the monitor by generating by a specialized software application a digital master folder representation of a patient's manual master folder, the digital master folder representation specifically designed for use as a graphical user interface by a radiologist;

d) said digital master folder representation providing data fields included within the digital master folder representation providing information and links to radiology reports and images regarding all radiology procedures associated with such patient stored in an information database in an electronic layout and color scheme conforming to the layout and color scheme of the patient's manual master folder and tailored to a radiology practice, such links providing for the viewing of additional information or images relating to a patient's medical records when clicked;

e) said viewing portal consisting of at least two monitors designed for the viewing of a plurality of radiology images including computer radiology, computer tomography, ultrasound, nuclear medicine, and magnetic resonance images, such images including current radiology images from a current radiology procedure being performed on the patient and images from prior radiology procedures; and f) said combination dictation and trackball device including a voice component that issues operational and navigational commands to the radiology portal and viewing portal by providing continuous speech recognition for the creation of dictated radiology reports.

18. The system of claim 17, wherein the radiology portal consists of a flat panel monitor and computer for the searching and viewing of medical information stored internal and external to the system.

19. The system of claim 17, wherein the radiology portal consists of a touch screen flat panel monitor and computer for searching and viewing of medical information stored internal and external to the system.

20. The system of claim 17, wherein the radiology portal consists of a flat panel monitor and computer with multi-processors for searching and viewing of medical information stored internal and external to the system.

21. The system of claim 17, wherein the radiology portal consists of a touch screen flat panel monitor and computer with multi processors for searching and viewing of medical information stored internal and external to the system.

22. The system of claim 17, wherein the viewing portal consists of a single high-resolution monitors design for the viewing of a plurality of radiology images including computer radiology, computer tomography, ultrasound, nuclear medicine, and magnetic resonance images.

23. The system of claim 17, wherein the viewing portal consists of a single high-resolution computer monitor.

24. The system of claim 17, wherein the viewing portal consists of two high-resolution computer monitors.

25. The system of claim 17, wherein the viewing portal consists of a four high-resolution monitors design for the viewing of a plurality of radiology images including computer radiology, computer tomography, ultrasound, nuclear medicine, and magnetic resonance images.

26. The system of claim 17, wherein the viewing portal includes six high-resolution monitors for the viewing of a plurality of radiology images including computer radiology, computer tomography, ultrasound, nuclear medicine, and magnetic resonance images.

27. The system of claim 17, wherein the viewing portal consists of eight high-resolution monitors design for the viewing of a plurality of radiology images including computer radiology, computer tomography, ultrasound, nuclear medicine, and magnetic resonance images.

28. The system of claim 17, wherein the combination dictation and trackball device includes a separate mouse and microphone.

* * * * *